US006600421B2

(12) United States Patent
Freeman

(10) Patent No.: US 6,600,421 B2
(45) Date of Patent: Jul. 29, 2003

(54) SYSTEM TO AUTOMATICALLY LOCALLY CONTROL A DEVICE ACCORDING TO PREFERENCES OF A USER ENTERING A LOCAL AREA OF THE DEVICE FROM A REMOTE AREA

(75) Inventor: Curtis W. Freeman, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/919,249

(22) Filed: Jul. 31, 2001

(65) Prior Publication Data
US 2003/0025604 A1 Feb. 6, 2003

(51) Int. Cl.[7] .............................................. G08B 23/00
(52) U.S. Cl. .................. 340/573.1; 340/3.31; 340/3.32; 340/5.1
(58) Field of Search ........................ 340/573.1, 870.01, 340/870.16, 3.1, 3.31, 5.8, 5.81, 5.1, 5.2, 3.32

(56) References Cited

U.S. PATENT DOCUMENTS

| 3,960,140 A | * | 6/1976 | Buxton ........................ 600/519 |
| 4,051,522 A | * | 9/1977 | Healy et al. ................... 358/86 |
| 4,958,645 A | | 9/1990 | Cadell et al. ................. 128/903 |
| 5,319,363 A | * | 6/1994 | Welch et al. ............ 340/825.36 |
| 5,594,786 A | * | 1/1997 | Chaco et al. .................... 379/93 |
| 5,687,734 A | * | 11/1997 | Dempsey et al. ............ 128/696 |
| 5,738,102 A | * | 4/1998 | Lemelson ..................... 128/671 |
| 5,748,103 A | * | 5/1998 | Flach et al. ............. 340/870.07 |
| 5,907,291 A | * | 5/1999 | Chen et al. ............. 340/870.16 |
| 5,960,085 A | * | 9/1999 | de la Huerga ................. 380/25 |
| 6,213,942 B1 | | 4/2001 | Flach et al. .................. 600/300 |
| 6,344,794 B1 | * | 2/2002 | Ulrich et al. ................. 340/539 |
| 2002/0013518 A1 | | 1/2002 | West et al. .................. 600/300 |

FOREIGN PATENT DOCUMENTS

| EP | 0505627 A2 | 9/1992 | ........... G06F/15/42 |
| EP | 1038497 A1 | 9/2000 | ............ A61B/5/00 |

* cited by examiner

Primary Examiner—Toan N Pham

(57) ABSTRACT

The present invention provides sensor generating measurement information based upon a patient parameter measured by the sensor and a processor managing local output of the measurement information according to automatically detected control signals locally and wirelessly transmitted from a transmitter entering a local area of the sensor from a remote area. The control signals include identification of a user and the transmitter travels with the user entering the local area of the sensor from a remote area so that the processor can manage local output of the measurement information according to stored preferences of the user. The processor can also control patient parameter measurements according to the preferences of the user.

22 Claims, 5 Drawing Sheets

SYSTEM TO AUTOMATICALLY LOCALLY CONTROL A DEVICE ACCORDING TO PREFERENCES OF A USER ENTERING A LOCAL AREA OF THE DEVICE FROM A REMOTE AREA

BACKGROUND OF THE INVENTION

1. Field of the Invention

The present invention relates to automatically locally controlling a monitoring device according to user preferences. In particular, the present invention relates to wirelessly and locally controlling a patient monitor according to clinician preferences upon presence of the clinician.

2. Description of the Related Art

A typical patient monitor generates measurement information by measuring patient parameters using sensors connected to a patient. Such parameters can include, for example, cardiovascular parameters and temperature. A typical monitor includes a local (near sensors of the patient monitor, bed/patient-side, in-room) output interface. The local output interface includes, for example, a display unit visually presenting measurements (e.g., a graphical or wave presentation), a recorder presenting the measurements in a print format, and a sound unit annunciating alarms or audibly providing the measurements. Therefore, the typical monitor can output the generated measurements to the local output interface for viewing, hearing and analysis by users (e.g., nurses and doctors).

A typical monitor also includes a local input interface. The local input interface includes, for example, a keypad to manually input information. The typical monitor also includes a processor executing software to generate the measurements and uses the measurements to perform various other processing functions, such as trending, archiving, reporting and diagnostics.

Patient monitoring environments include, for example, centrally controlled bed-side patient monitors and standalone bed-side patient monitors. In a typical system environment the monitors are located in patient rooms. In case of the centrally controlled bed-side monitors, the monitors include a communication interface for communicating measurements and other information to other devices, such as a central computer (i.e., a remote controller or a remote patient-monitor output interface). For example, a central computer can be connected via a network (wire or wireless) to each monitor via the communication interface of the monitor. The central computer can, for example, be located at the nurse station in a hospital. A typical central computer includes a local (computer-side, in-room) output interface.

A patient monitor is typically controlled as follows: personnel (e.g., nurses) at the nurse station can manually input commands at the central computer to control each monitor. Further, commands can be manually input via the local input interface of the monitor to control the monitor. Monitor control functions can include, for example, commands manually input to set and adjust monitoring and local measurement output configurations, and to control transmission of the measurements to the central computer via the communication interface of the monitors. For example, a monitor's local measurement output configuration can be set to sleep mode by turning off local output of sound and display.

However, manually controlling the patient monitor, either centrally using the central computer input interface or locally using the local input interface of the patient monitor, has the following disadvantage: personnel may forget to set and adjust local measurement output configurations and monitoring configurations. For example, although local, in-room, patient-side or central-computer-side, output of measurements is useful to trained personnel, such as doctors and nurses, such information may not be useful or necessary to the patient and all personnel (as the case may be). Further, local display and annunciation of alarms when no trained staff is in the patient room or with the patient is not only unnecessary, but can often cause much anxiety for the patient, family or friends visiting the patient. Further, while local, in-room, patient-side, or central-computer-side, display of certain information may be useful and preferable by some nursing staff, the same information may not be useful or preferred by all nursing staff or the physician staff, thereby requiring manual control by each person. Therefore, there is a need to automatically locally (e.g., in-room, patient-side, or central-computer-side) set and adjust local measurement output configurations and monitoring configurations.

SUMMARY OF THE INVENTION

The present invention can be attained by a patient monitor comprising sensors monitoring parameters of a patient and generating measurements (information) based upon the monitoring, a local output interface outputting the measurements, a detector wirelessly detecting information signals from a local transmitter, and a processor managing output of the measurements to the local output interface according to the detected information. Therefore, the present invention can provide placing in a room a bed-side (patient side) patient monitor that manages (such as activating, deactivating, adjusting) local output of measurements based upon monitoring of the patient parameters when a clinician is in the room, upon approach/entry of the clinician to/in the room, or when the clinician enters a local area (i.e., within a predetermined short distance/range) of the bed-side monitor.

More particularly, the present invention provides an apparatus comprising a sensor generating measurement information based upon a patient parameter measured by the sensor, and a processor managing local output of the measurement information according to automatically detected control signals locally and wirelessly transmitted from a transmitter entering a local area of the sensor from a remote area. The control signals include identification information of a user and the transmitter travels with the user entering the local area from the remote area.

Further, the present invention can be attained by a patient-monitor remote controller (i.e., a central computer or a remote patient-monitor output interface) comprising a communication interface transmitting/receiving information via a network (wireless or wire) to/from a patient monitor, the information including measurements from monitoring a patient parameter by the patient monitor and commands to control the patient monitor from the remote controller, a local output interface outputting received measurements, a detector wirelessly detecting information signals transmitted from a local transmitter, and a processor managing output of the received measurements to the local output interface according to the detected information. Therefore, the present invention can provide a patient-monitor remote controller that automatically manages (such as activating, deactivating, adjusting) local output of a patient parameter measurement received by the remote controller from a patient monitor controlled by the remote controller when a clinician enters a local area (i.e., within a predetermined short distance/range) of the remote controller.

More particularly, the present invention provides an apparatus comprising a communication interface transmitting/receiving information via a network to/from a patient monitor, the information including measurements from monitoring a patient parameters by the patient monitor, and a processor managing local output of the received measurements according to automatically detected control signals locally and wirelessly transmitted from a transmitter entering a local area of the apparatus from a remote area. The control signals include identification information of a user and the transmitter travels with the user entering the local area from the remote area.

Further, the present invention can be attained by a patient monitor automatically managing local output of the patient parameter measurement information according to preferences of users. The patient monitor manages the local output of the measurements to a local display unit, a local sound unit and a local recorder in communication with the apparatus, the local display unit locally displaying the measurements in various formats (e.g., graphically, wave format), the local sound unit locally annunciating alarms and providing audible information based upon the measurements, and the local recorder locally printing the measurements.

Further, the present invention can be attained by a patient-monitor remote controller automatically managing, according to preferences of users, local output of measurements received from a patient monitor controlled by the remote controller.

Further, the present invention can be attained by a patient monitor automatically controlling sensors to monitor parameters of a patient according to preferences of users.

Further, the present invention can be attained by a patient-monitor remote controller automatically controlling sensors of a patient monitor controlled by the remote controller to monitor parameters of a patient according to preferences of users.

Further, the present invention can be attained by a method of monitoring parameters of a patient, generating measurement information based upon the monitoring, locally outputting the measurement information, wirelessly detecting information signals from a local transmitter, and managing the outputting according to the detected information. Therefore, the present invention provides generating measurements based upon a patient parameter measured by a sensor, automatically detecting locally and wirelessly transmitted control signals from a transmitter entering a local area of the sensor, and managing local output of the measurements according to the control signals. The control signals include identification of a user and the transmitter is traveling with a user entering the local area from the remote area.

Further, the present invention can be attained by a transmitter wirelessly in communication with a patient monitor when within a predetermined distance from the patient monitor, the patient monitor including a detector automatically and wirelessly detecting information signals from the transmitter when the transmitter enters a local area of the patient monitor, the local transmitter comprising a processor transmitting the information signals, including identification of a user, to the detector, wherein the patient monitor manages local output of measurements from monitoring a patient parameter by the patient monitor according to preferences of the user. Therefore, the present invention provides a transmitter comprising a transmission unit and a processor wirelessly and automatically transmitting control signals via the transmission unit for automatic detection by a patient monitor when the transmitter enters a local area of the patient monitor. The patient monitor manages local output of measurements based upon a patient parameter measured by the patient monitor according to the control signals detected by the patient monitor. The control signals include identification of a user or user preferences and the transmitter is traveling with the user entering the local area from a remote area. The transmitter further comprises a storage unit storing the identification information of the user and preferences of the user.

Further the present invention can be attained by a system comprising a transmitter transmitting control signals, and an apparatus comprising a sensor generating measurements based upon a patient parameter measured by the sensor and a processor managing local output of the measurements according to the automatically detected control signals locally and wirelessly transmitted from the transmitter entering a local area of the sensor from a remote area. More particularly, the present invention provides a sensor generating measurements based upon a patient parameter measured by the sensor, a transmitter transmitting control signals and entering a local area of the sensor from a remote area and a processor managing local output of the measurements according to the control signals automatically detected upon the entering of the transmitter to the local area of the sensor. The transmitter travels with a user entering the local area from the remote area.

BRIEF DESCRIPTION OF THE DRAWINGS

The advantages of the invention will become apparent and more readily appreciated from the following description of the preferred embodiments, taken in conjunction with the accompanying drawings of which.

DETAILED DESCRIPTION

Figure 1:
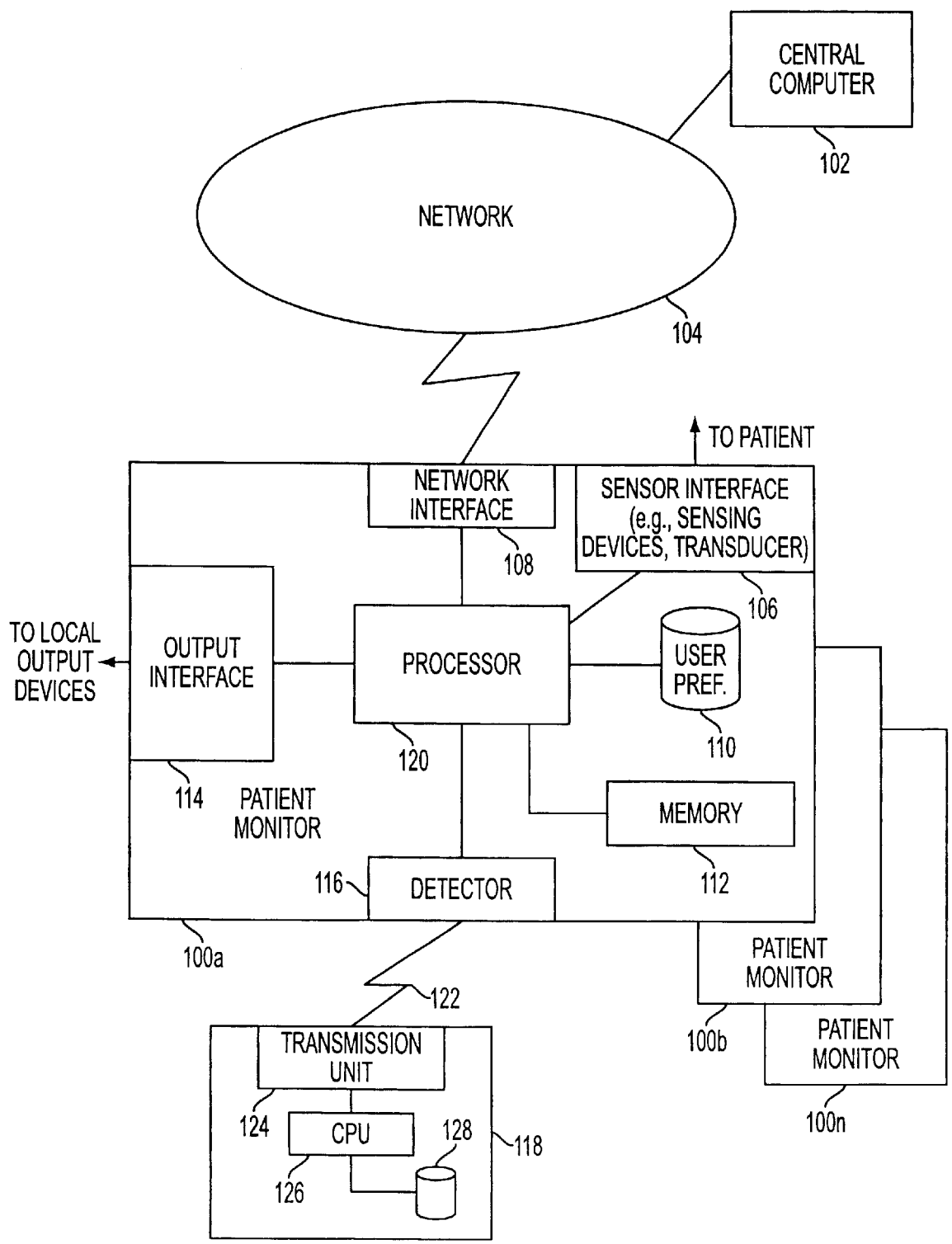
FIG. 1 is a block diagram of a patient monitoring system according to the present invention.

Reference will now be made in detail to the present preferred embodiments of the present invention, examples of which are illustrated in the accompanying drawings, wherein like reference numerals refer to the like elements throughout. The embodiments are described below to explain the present invention by referring to the figures.

FIG. 1 is a block diagram of a patient monitoring system according to the present invention. Referring to FIG. 1, apparatuses 100a–100n are patient monitors in communication with central computer (patient-monitor remote controller) 102 via network 104. The network 104 can be wire or wireless having a conventional topology and a conventional architecture. The architecture of network 104 can, for example, be client-server using conventional communication protocols. The network 104 can, for example, be a local area network or a wide area network, such as the Internet. The central computer 102 can be a conventional computer or computing device capable of storing, displaying and processing information, and communicating with patient monitors 100a–100n by receiving and transmitting information via the network 104 using conventional techniques.

A patient monitor 100 has a sensor interface (unit) 106 to monitor and generate measurement information based upon a patient parameter measured by the sensor interface connected to a patient. The sensor interface provides sensors, such as transducers and other sensing devices to monitor and generate measurement information based upon the parameters of the patient measured by the sensors. A patient's parameters can, for example, be cardiovascular parameters and temperature. A processor 120 is in communication with and executes software to control sensor interface 106 and manage the measurement information generated by sensor interface 106.

Storage devices 110 and 112 that store information, such as memory, hard drives, or drives for removable media (e.g., CD-R, CD-ROM, CD-RW, DVD-ROM and DVD-RAM) may be connected to each patient monitor 100a–100n by conventional techniques to provide local storage for patient monitor 100. Each patient monitor 100a–100n includes a local output interface 114. The local output interface 114 provides interfaces with local output devices for local information output. The local output interface 114 can include, for example, a local display unit (not shown), a local audio unit (not shown), a local recorder (printer) (not shown) and an input/output unit for communication with other local equipment. A local input interface, such as a keyboard (not shown) can provide manual command input for the patient monitor 100.

Each patient monitor 100a–100n further includes a detector 116. The detector 116 uses wireless technology 122 to automatically detect control/information signals locally transmitted from a transmitter 118 when the transmitter comes within a predetermined distance from the detector 116. When the transmitter 118 enters a local area of the sensors 106 from a remote area, the detector 116 automatically detects wireless control signals transmitted by the transmitter 118. The local area can be defined, for example, as a room in which the patient is being monitored or a predetermined short distance, such as 20 feet radius, from sensor interface 106 (the bed-side patient monitor 100) according to system and application design specifications. The local area can also be defined according to or within applicable communication distance specifications of the particular wireless technology 122 used, such as 10 meters according to Bluetooth wireless technology specification. Preferably the detection system operates within a limited range so that signals transmitted from other transmitters 118, for example, outside of a room are detected infrequently. The detector 116 and transmitter 118 can use wireless technology 122 (detection system) such as infrared technology (e.g., IrDA standard) and radio technology. Radio technologies can include, for example, wireless networking (e.g., IEEE 802.11 B standard), local radio frequency (RF) (e.g., Bluetooth and HomeRF standards) and Ultra-Wideband Radio (UWB).

Preferably detector 116 and transmitter 118 use wireless radio frequency technology because of radio frequency's better omni-directional communication capability than infrared's (IR) line-of-sight communication capability. For example, IR signals can be lost if the user traveling with the transmitter 118 turns his/her back to the detector 116, or the transmitter 118 is covered, for example, by clothing. Further, preferably detector 116 and transmitter 118 use wireless radio frequency that operates at the 2.4 GHz—the Industrial-Scientific-Medical (ISM) band. Further, preferably wireless technology 122 limits interference with other devices operating in the ISM band. Further, preferably detector 116 and transmitter 118 cause minimal, if any, electromagnetic interference with other electronic equipment/devices. Further, preferably wireless technology 122 supports automatic linking (i.e., establishing communication) when transmitter 118 comes into a specified distance range of detector 116.

In the preferred embodiment, detector 116 and transmitter 118 use the commercially available Bluetooth wireless technology because such technology is known to limit interference with other devises operating in the ISM band as well as cause minimal electromagnetic interference with other electronic devices. The Bluetooth wireless technology is low-power (1 milliwatt), short range (10 meters), can operate at the 2.4 GHz ISM band and supports automatic linking between mobile devices.

Each patient monitor 100a–100n can include a network interface 108 communicating, using conventional techniques, with the central computer 102 via the network 104. The network interface 108, local output interface 114, storage devices 110 and 112, and detector 116 can be integrated with the patient monitor or locally external to patient monitor 100 and in communication with patient monitor 100 using conventional techniques. The processor 120 can be one or more processing units integrated with or external to patient monitor 100. In case of being external, processor 120 would be local and in communication with patient monitor 100 using conventional interfaces and techniques. Software of an existing patient monitor can be modified to incorporate the processes of the present invention. Alternatively, a local external processing unit 120, which is in communication with the patient monitor and a local external detector 116, can execute software implementing the processes of the present invention, obviating modifying existing patient monitor software.

The processor 120 is in communication with and executes software to control the network interface 108, the storage devices 110 and 112, the local output interface 114 and the detector 116, using conventional techniques, so that patient monitors 100a–100n can automatically detect the presence of a clinician, such as a doctor or nurse, in the immediate area of the patient monitor, typically a patient room, and assume a "personality" consistent with the clinician's role. A patient monitor 100 can also assume an appropriate "personality" when no clinical staff is in the vicinity by providing customized default configurations.

Transmitter 118 includes a transmission unit 124 wirelessly transmitting information signals for automatic detection by detector 116. As discussed above, transmission unit 124 can use RF and IR wireless technology 122. In one embodiment, transmitter 118 can include a processor 126 executing software controlling transmitter 118 according to the present invention. Transmitter 118 can also include a storage unit 128. The storage unit 128 can be conventional memory storing user information, such as user identification information and user preferences. The transmitter 118 can use conventional techniques for power, such as a battery.

Figure 2:
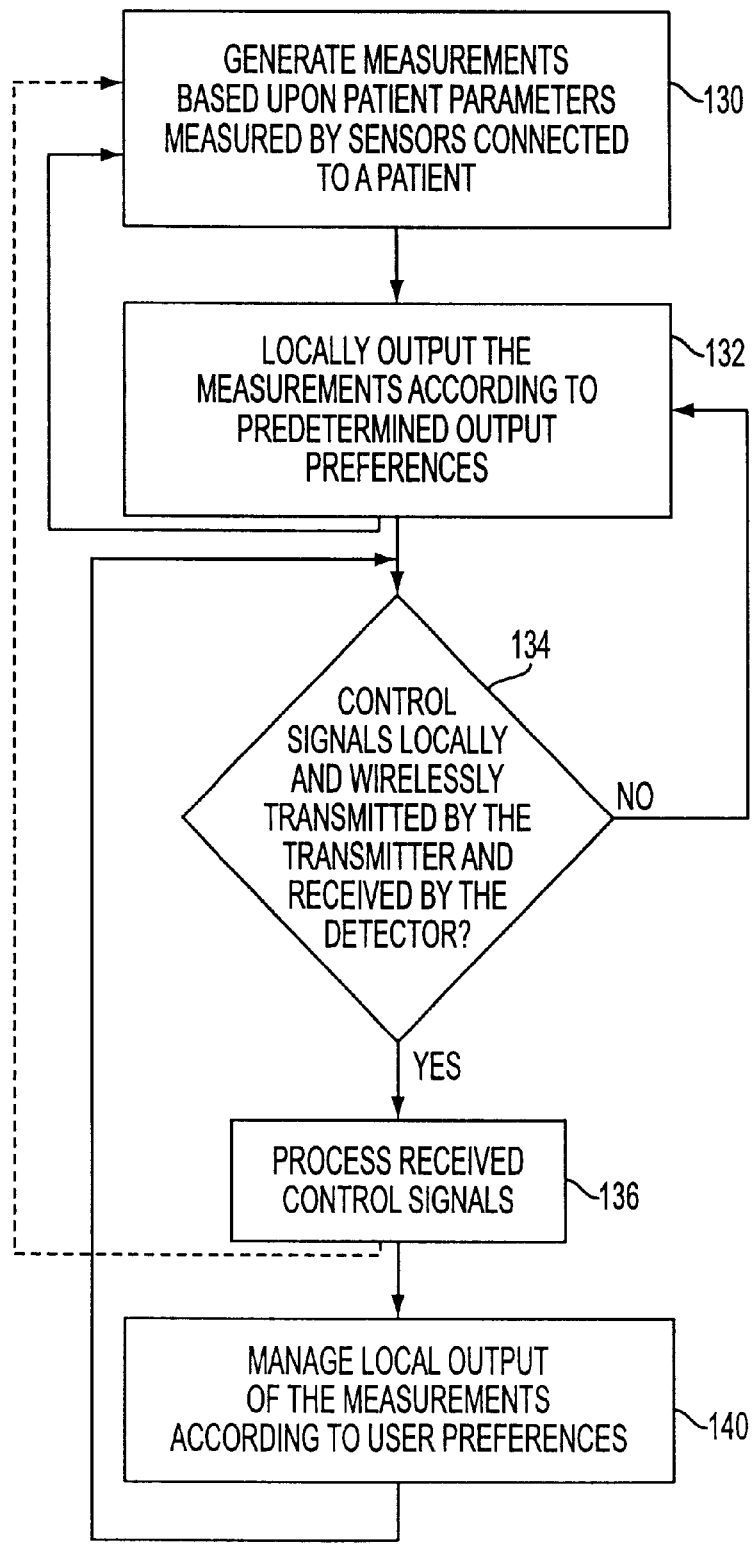
FIG. 2 is a flow chart of operations in a preferred embodiment of the present invention.

FIG. 2 is a flow chart of operations in a preferred embodiment of the present invention. The processes according to embodiments of the present invention can be implemented in software controlling patient monitors 100a–100n and transmitter 118 to perform the processes. Referring to FIG. 2, at 130 a sensor 106 of patient monitor 100 generates measurements based upon a patient parameter measured by sensor 106. At 132 the patient monitor 100 locally outputs the measurements to local output interface 114 of the patient monitor according to predetermined output preferences (output configurations) when no user is in a local area of the patient monitor 100. For example, because there is no clinician in the local area of the patient monitor, preset configurations would provide that local display and annunciation of alarms be suspended, dimmed, or lowered, or that the patient monitor be in power-save mode. When a clinician is not present, there is little reason to have patient parameter measurements output because no one is present to interpret the measurements. Display and annunciation of such measurements when no trained staff is in the room is not only unnecessary, but often can cause much anxiety for the patient or family and friends visiting the patient. A monitor that dims/blanks its display and suppresses alarms and other tones when not needed would allow the patient to better sleep or rest.

At 134, detector 116 of patient monitor 100 continuously checks for control signals locally and wirelessly transmitted from transmitter 118. The detector 116 automatically detects control signals locally and wirelessly transmitted from transmitter 118 entering a local area of the patient monitor from a remote area. The transmitter 118 can, for example, be traveling (i.e., worn) by a clinician. At 136, patient monitor 100 processes the received control signals. At 140, the patient monitor 100 manages local output of the measurements according to the automatically detected control signals. The patient monitor 100 can store in storage unit 110 user preferences of clinicians, such as measurement output preferences. If the control signals include identification information of the clinician, then at 136 patient monitor 100 identifies the clinician and accesses the clinician preferences stored in storage unit 110. At 140, patient monitor 100 manages local output of the measurements according to the stored preferences of the clinician. The transmitter 118 can also store in storage unit 128 clinician preferences, such as measurement output preferences. If transmitter 118 stores the clinician preferences, transmitter 118 would transmit the preferences as control signals for processing by patient monitor 100.

Therefore, transmitter 118 wirelessly and automatically transmits control signals for automatic detection by a patient monitor 100 when the transmitter traveling with user enters a local area of the patient monitor. Upon detection of the control signals, the patient monitor manages according to the control signals local output of measurements based upon a patient parameter measured by the patient monitor. If the control signals include identification of the user, patient monitor 100 identifies the user and reads the user's preferences from storage unit 110 and manages output of the measurement according to the user's preferences. If the control signals include the user's preferences read from storage unit 128 of transmitter 118, patient monitor 100 manages output of the measurement according to the user's preferences.

In another embodiment, at 136 (dashed line) patient monitor 100 can control sensor interface 106 to monitor the parameters of the patient according to the automatically detected control signals and user preferences at 134. In another embodiment, at 136 patient monitor 100 can generate diagnostic information and archive the measurement information according to the automatically detected control signals and user preferences at 134.

When transmitter 118 leaves the local area of patient monitor 100, detector 116 would not detect at 134 any locally and wirelessly transmitted control signals. If control signals are not detected at 134, the monitor configurations are reset to the default settings at 132. The default settings can be a quiescent state. A delay period can be provided, during which no signal is received by detector 116, before going to the "quiet" state.

In another embodiment, software controlling the patient monitor 100 is configured to detect at 134 a "valid" control signal from transmitter 118 for a prescribed time before processing the control signal and changing any monitor conditions. This could help in situations where a clinician traveling with transmitter 118 passing a room with a patient monitor of the present invention would not immediately or inadvertently trigger a monitor condition change.

In another embodiment, software controlling the patient monitor 100 would detect different signals that would correspond to an individual or a user group. The patient monitor 100 could then employ different measurement output configuration sets, providing the monitor a personality consistent with the local clinician's role. For example, the nursing staff may have a preferred display of certain patient parameters while a cardiologist may have a different preferred display of parameters. Nurses on the night shift may desire a different behavior than the day shift, triggered by a different badge ID or a combination of badge ID and local time.

In another embodiment, software controlling the patient monitor 100 accommodates/resolves conflicts according to applicable design specifications when detector 116 detects control signals from two or more transmitters 118. For example, the software can resolve conflicts by determining which received control signal takes precedence and managing local output of the measurement information according to the control signals with precedence.

Advantages of the present invention are as follows: the present invention provides automatically changing the patient monitor configuration, such as output of parameter measurements and which parameters to measure, to match the needs of the clinical situation in the patient's room or patient's local area. Clinicians get the monitor "personality" or configuration best suited for their job. Further, patient and family anxiety can be reduced by, for example, suspending local alarms, printing and displays. Further, "nurse call" interruptions to the clinical staff can be reduced from concerned but untrained patients and visitors. Further, dimming/power-saving the monitor at night or when no one is present to use the measurements output can accommodate energy savings. Of course, in case of a centrally controlled patient monitoring environment, patient monitoring as well as output of respective patient parameter measurements can be maintained at normal, required or default configuration remotely at central computer 102 (i.e., nurse central stations). In case of standalone patient monitoring environments, patient monitoring can be maintained at normal, required or default configuration with only measurement output configurations adjusted for when no clinician is in the local area of the patient monitor.

Figure 3:
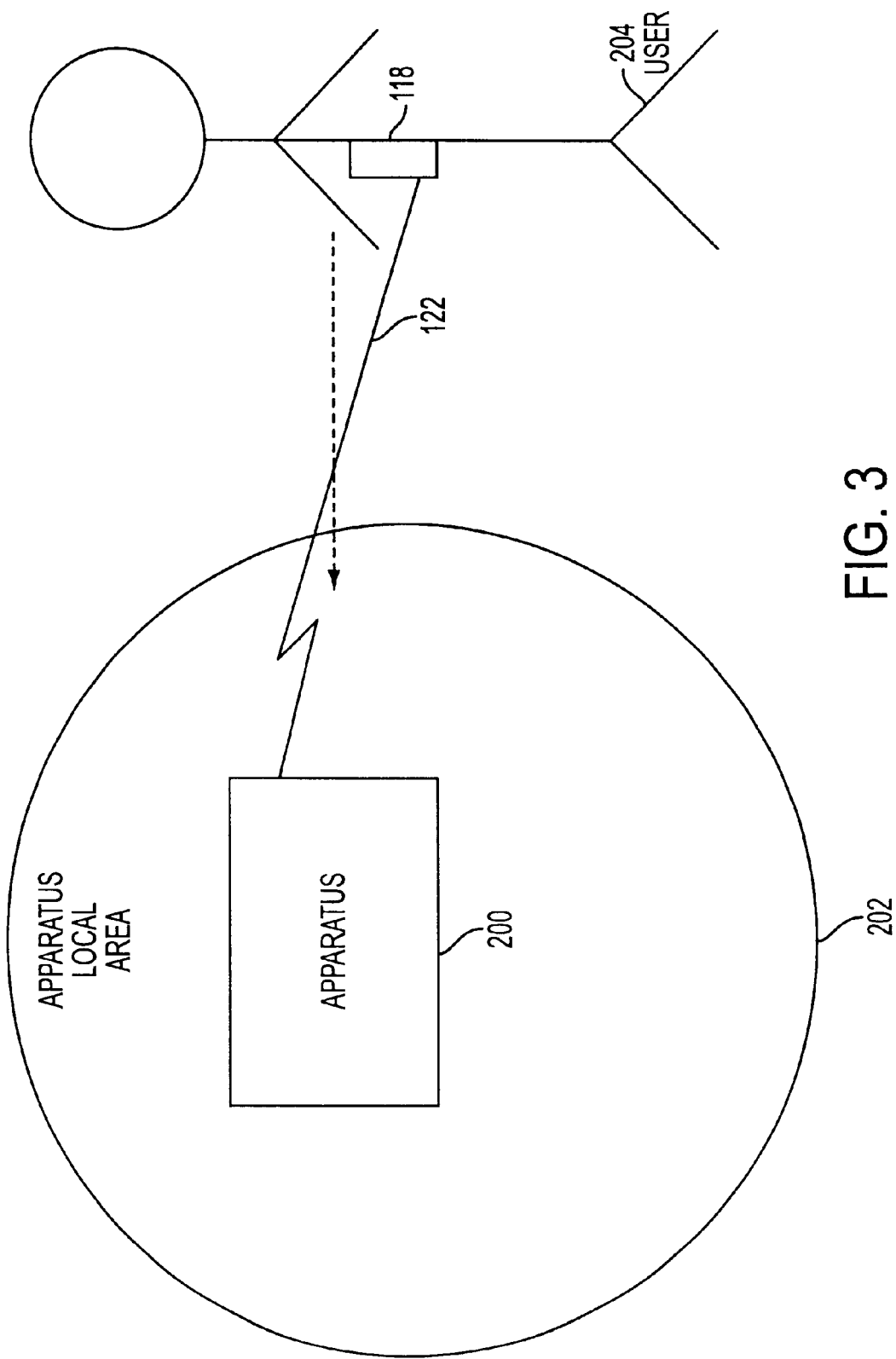
FIG. 3 is a block diagram of a patient monitoring system as used according to the present invention.

FIG. 3 is a block diagram of a patient monitoring system as used according to the present invention. Apparatus 200 outputs measurements based upon a patient parameter measured by a sensor connected to a patient (not shown) and the measurement output is managed according to automatically detected control signals locally and wirelessly transmitted from transmitter 118 entering a local area 202 of the apparatus from a remote area. The transmitter 118 and apparatus 200 use wireless technology 122. The transmitter 118 is traveling with a user 204 entering the local area from the remote area. Apparatus 200 is in communication with the sensor connected to the patient (not shown).

Figure 4:
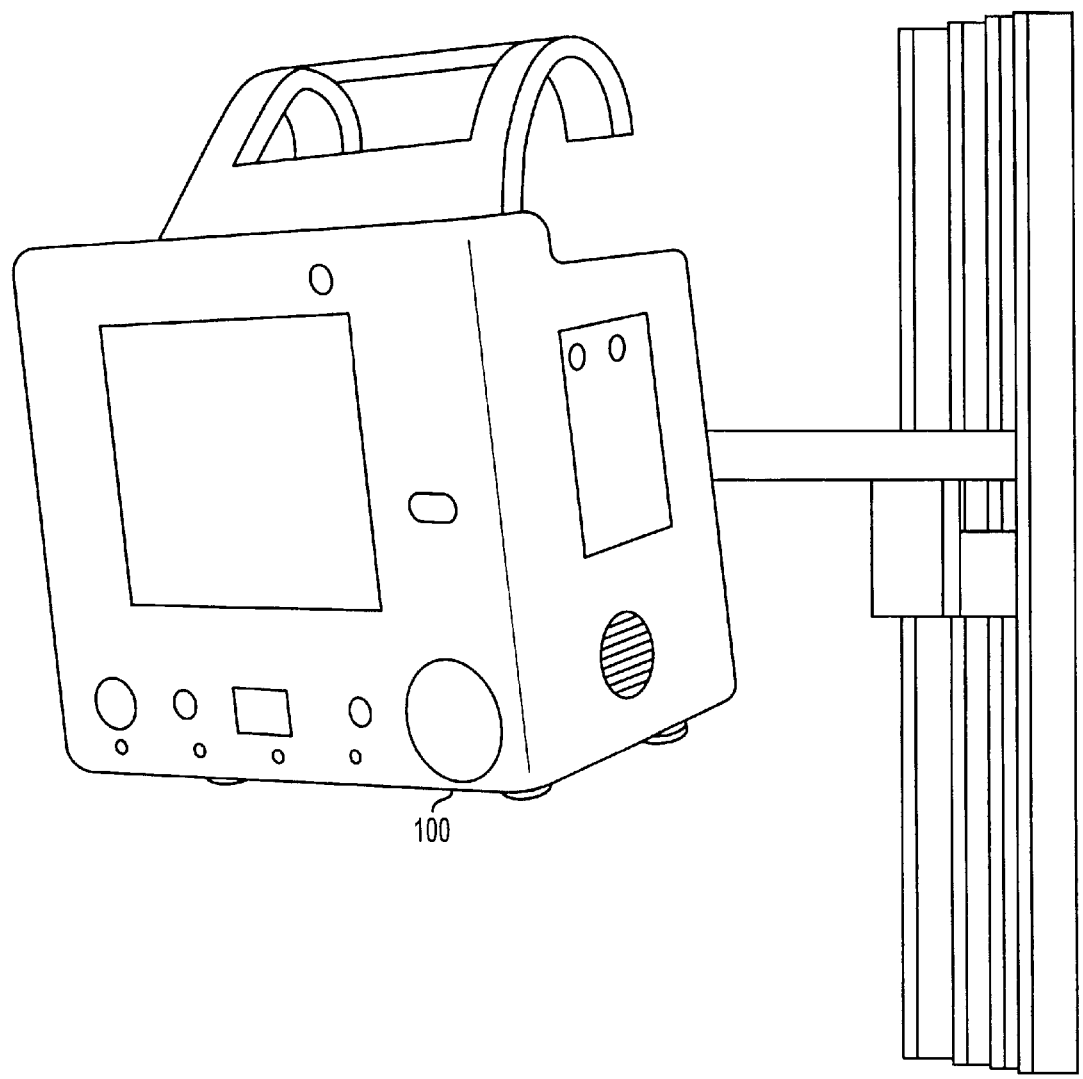
FIG. 4 is an image of an exemplary patient monitor.

FIG. 4 is an image diagram of a patient monitor 100 in which the present invention is implemented. Such patient monitors are available from Agilent Technologies, Inc. Palo Alto, Calif., assignee of the present application, under the tradenames A1 and A3™ compact patient monitors.

Figure 5:
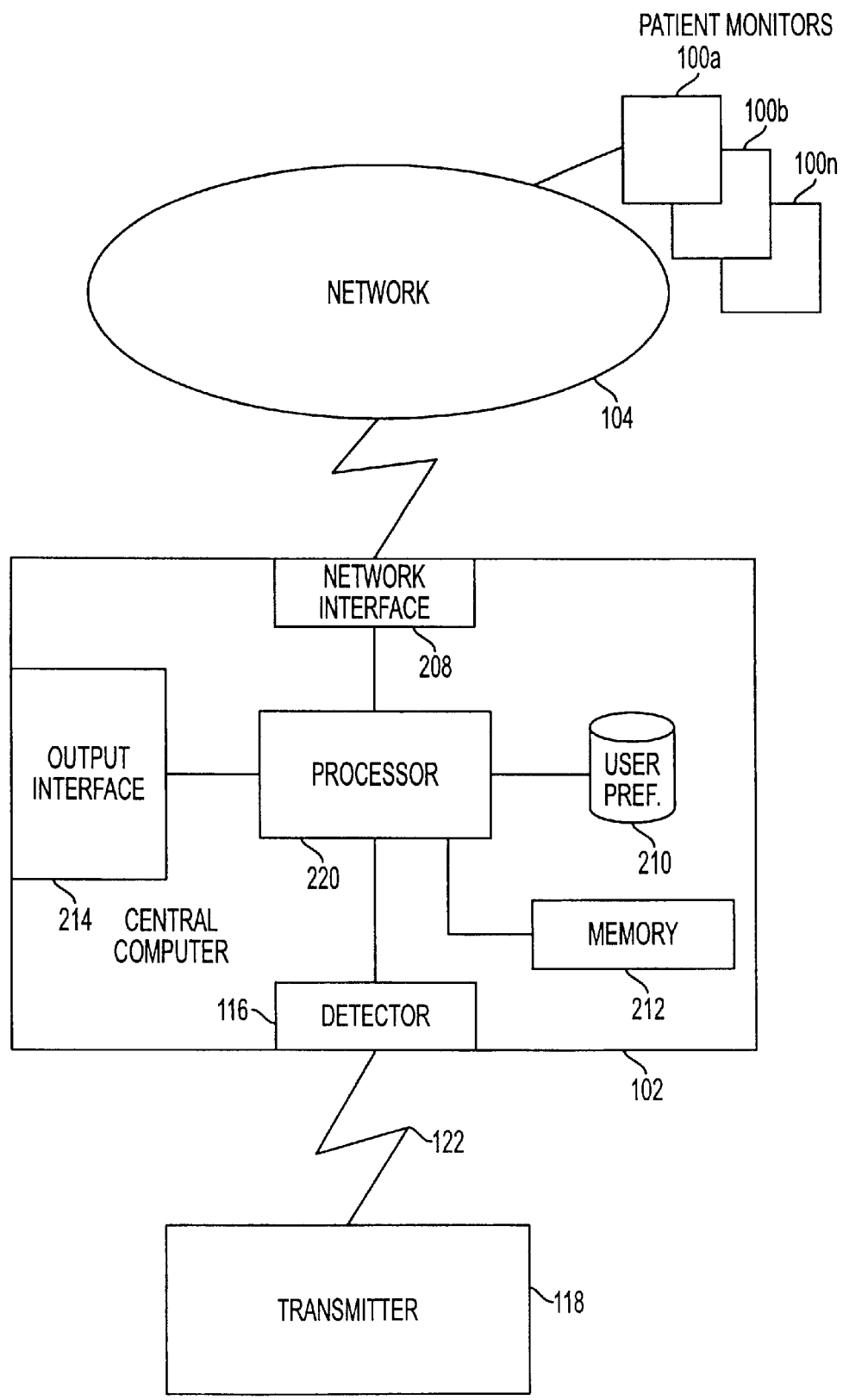
FIG. 5 is a block diagram of a patient-monitor remote controller according to the present invention

FIG. 5 is a block diagram of a patient-monitor remote controller (i.e., the central computer in a patient monitoring environment or the nurse's station) according to the present invention. In another preferred embodiment of the present invention, the remote controller 102 has a network interface 208 communicating with patient monitors 100a–100n via network 104 and a local output interface 214. The local output interface 214 provides interfaces with local output devices for local information output. The local output interface 214 can include, for example, a local display unit (not shown), a local audio unit (not shown), a local recorder (printer) (not shown) and an input/output unit for communication with other local equipment. A local input interface, such as a keyboard (not shown) can provide manual command input for remote controller 102.

A processor 220 is in communication with and executes software to control network interface 208 transmitting/receiving information via the network 104 to/from patient monitors 100a–100n. The information communicated between remote controller 102 and patient monitor 100 includes measurement information from monitoring a patient parameters by the patient monitor 100 as well as commands input at remote controller 102 to control patient monitor 100. Therefore, remote controller 102 can be used to remotely control patient monitor 100 and manage local output of a patient parameter measurement received by the remote controller from the patient monitor via network interface 208.

Storage devices 210 and 212 that store information, such as memory, hard drives, or drives for removable media (e.g., CD-R, CD-ROM, CD-RW, DVD-ROM and DVD-RAM) may be connected to remote controller 102 by conventional techniques to provide local storage.

The remote controller 102 further includes detector 116 as discussed above in connection with patient monitor 100 (FIG. 1). The detector 116 uses wireless technology 122 to automatically detect control/information signals locally transmitted from transmitter 118 when the transmitter comes within a predetermined distance from the detector 116. When transmitter 118 enters a local area of remote controller 102 from a remote area, detector 116 automatically detects wireless control signals transmitted by transmitter 118. The remote controller 102 can manage local output of the measurement information received from patient monitor 100 according to the automatically detected control signals, which can include user identification information and user output preferences.

The network interface 208, storage devices 210 and 212, and detector 116 can be integrated with remote controller 102 or locally external to remote controller 102 and in communication with remote controller 102 using conventional techniques. Software of an existing remoter controller 102 can be modified to incorporate the processes of the present invention. Alternatively, a local external processing unit 220, which is in communication with remote controller 102 and a local external detector 116, can execute software implementing the processes of the present invention, obviating modifying existing remote controller 102 software.

The processor 220 is in communication with and executes software to control the network interface 208, the storage devices 210 and 212, the local output interface 214 and the detector 116, using conventional techniques, so that remote controller 102 can automatically detect the presence of a clinician, such as a doctor or nurse, in the immediate area of the remote controller, typically at the nurse station, and assume a "personality" consistent with the clinician's role. A remote controller 102 can also assume an appropriate "personality" when no clinical staff is in the vicinity by providing customized default configurations.

The remote controller 102 manages local output of measurements received from a remote patient monitor 100 according to automatically detected control signals locally and wirelessly transmitted from transmitter 118 entering a local area of remoter controller 102 from a remote area. The transmitter 118 travels with a user entering the local area from the remote area. The nurse's central station 102 can also control remote patient monitors 100 according to the automatically detected control signals. The control signals include, for example, identification information of a user and user preferences. Operation of remote controller 102 can be same as operation of a patient monitor 100 according to the present invention as illustrated in FIG. 2 and description thereof above.

Typically, a nurse's central station 102 always displays patient parameter measurements and annunciates alarms for multiple patients simultaneously even when no one is at the patients' bedside or the local output of the bedside patient monitors are in sleep mode. Therefore, according to the present invention, for example, detector 116 of nurse's central station 102 can detect presence of a particular nurse/doctor entering a local area of the nurse's station and the nurse-station's local outputs could be adjusted to provide more information on a particular set of monitored patients, such as the detected clinician's patients.

The present invention provides a sensor generating measurements based upon a patient parameter measured by the sensor, a transmitter transmitting control signals and entering a local area of the sensor from a remote area, and a processor managing local output of the measurements according to the control signals automatically detected upon the entering of the transmitter to the local area of the sensor. The transmitter travels with a user entering the local area from the remote area. The present invention further provides a storage unit storing preferences of the user and the processor can manage the local output of the measurements according to the preferences of the user, can control the sensor according to the preferences of the user and can generate diagnostics based upon the measurements according to the preferences of the user.

The present invention can also provide a communication interface transmitting/receiving information via a network to/from a patient monitor, the information including measurement information from monitoring a patient parameter by the patient monitor, a transmitter transmitting control signals and entering a local area of the communication interface from a remote area, and a processor managing local output of the measurement information received by the communication interface according to control signals automatically detected upon the entering of the transmitter to the local area of the communication interface.

The present invention is not limited to a particular placement of a controller (processor) that provides intelligence by executing software and detector 116, which uses wireless technology 122 to automatically detect control/information signals locally transmitted from transmitter 118 when the transmitter enters a local area of detector 116. For example, (1) the controller and detector could be built into bedside patient monitor 100, (2) the controller could be built into the bedside patient monitor 100 and the detector could be separate but wired directly to the bedside patient monitor 100, (3) the controller and the detector could form a separate device with a network connection that controls the bedside patient monitor 100 via the network; (4) the controller and the detector could be built into nurse's station 102 to process detected signals and control the nurse station's local outputs;

and (5) the controller and the detector could form a separate device but wired directly to nurse's station 102 to process detected signals and control the nurse-station's local outputs.

Although a few preferred embodiments of the present invention have been shown and described, it would be appreciated by those skilled in the art that changes may be made to the embodiments without departing from the principles and spirit of the invention, the scope of which is defined in the claims and their equivalents.

What is claimed is:

1. An apparatus, comprising:
   a sensor generating measurement information based upon a patient parameter measured by the sensor;
   a processor managing local output of the measurement information according to automatically detected control signals locally and wirelessly transmitted from a transmitter entering a local area of the sensor from a remote area; and
   a storage unit storing preferences of the user and the control signals include identification information of the user, the processor managing the local output of the measurement information according to the preferences of the user based upon identifying the user from the control signals.

2. The apparatus according to claim 1, wherein the transmitter is traveling with a user entering the local area from the remote area.

3. The apparatus according to claim 2, wherein the control signals include preferences of the user and the processor manages the local output of the measurement information according to the preferences of the user.

4. The apparatus according to claim 1, wherein the processor manages the local output of the measurement information to a local display unit, a local sound unit and a local recorder in communication with the apparatus, the local display unit locally displaying the measurement information, the local sound unit locally annunciating alarms and providing audible information based upon the measurement information, and the local recorder locally printing the measurement information.

5. The apparatus according to claim 1, wherein the processor further uses the measurement information to generate diagnostic information and archives the measurement information according to the control signals.

6. The apparatus according to claim 1, wherein the processor further uses the measurement information to generate diagnostic information and archives the measurement information according to the preferences of the user.

7. The apparatus according to claim 1, wherein the processor further controls the sensor to monitor the parameter of the patient according to the control signals.

8. The apparatus according to claim 1, wherein the processor further controls the sensor to monitor the parameter of the patient according to the preferences of the user.

9. The apparatus according to claim 1, wherein the local area is a room or a predetermined short distance from the sensor.

10. A system, comprising:
    a sensor generating measurements based upon a patient parameter measured by the sensor;
    a transmitter transmitting control signals and entering a local area of the sensor from a remote area;
    a processor managing local output of the measurements according to the control signals automatically detected upon the entering of the transmitter to the local area of the sensor; and
    a storage unit storing preferences of the user and the control signals include identification information of the user, the processor managing the local output of the measurements according to the preferences of the user based upon identifying the user from the control signals.

11. The system according to claim 10, wherein the transmitter is traveling with a user entering the local area from the remote area.

12. The system according to claim 11, wherein the control signals include preferences of the user and the processor manages the local output of the measurements according to the preferences of the user.

13. The system according to claim 10, wherein the processor further uses the measurements to generate diagnostic information and archives the measurements according to the control signals.

14. The system according to claim 10, wherein the processor further uses the measurements to generate diagnostic information and archives the measurements according to the preferences of the user.

15. The system according to claim 10, wherein the processor further controls the sensor to monitor the parameter of the patient according to the control signals.

16. The system according to claim 10, wherein the processor further controls the sensor to monitor the parameter of the patient according to the preferences of the user.

17. A transmitter, comprising
    a processor wirelessly and automatically transmitting control signals for automatic detection by a patient monitor when the transmitter enters a local area of the patient monitor, the patient monitor managing according to the control signals local output of patient parameters measured by the patient monitor; and
    a storage unit storing preferences of a user and the control signals includes the preferences of the user.

18. The transmitter according to claim 17, wherein the transmitter is traveling with a user entering the local area from a remote area.

19. An apparatus, comprising:
    a communication interface transmitting/receiving information via a network to/from a patient monitor, the information including measurements from monitoring a patient parameter measured by the patent monitor;
    a processor managing local output of the measurements received by the communication interface according to automatically detected control signals locally and wirelessly transmitted from a transmitter entering a local area of the sensor from a remote area; and
    a storage unit storing preferences of the user and the control signals include identification information of the user, the processor managing the local output of the measurement information according to the preferences of the user based upon identifying the user from the control signals.

20. The apparatus according to claim 19, wherein the transmitter is traveling with a user entering the local area from the remote area.

21. The apparatus according to claim 19, wherein the processor further controls the patient monitor according to the control signals.

22. The apparatus according to claim 19, wherein the processor further controls the patient monitor according to the preferences of the user.

* * * * *